(12) United States Patent
Wang et al.

(10) Patent No.: US 12,285,540 B2
(45) Date of Patent: *Apr. 29, 2025

(54) HEMOSTATIC COMPOSITE AGGREGATE MATERIALS HAVING SURFACE ENRICHED WITH HEMOSTATIS-PROMOTING AGENTS

(71) Applicant: Ethicon, Inc., Somerville, NJ (US)

(72) Inventors: Yi-Lan Allen Wang, Somerville, NJ (US); Jerry Yan, Hillsborough, NJ (US); Leo B. Kriksunov, Ithaca, NY (US)

(73) Assignee: Ethicon, Inc., Raritan, NJ (US)

( * ) Notice: Subject to any disclaimer, the term of this patent is extended or adjusted under 35 U.S.C. 154(b) by 900 days.

This patent is subject to a terminal disclaimer.

(21) Appl. No.: 16/934,998

(22) Filed: Jul. 21, 2020

(65) Prior Publication Data

US 2022/0023491 A1    Jan. 27, 2022

(51) Int. Cl.
*A61L 26/00* (2006.01)

(52) U.S. Cl.
CPC ....... *A61L 26/0066* (2013.01); *A61L 26/0038* (2013.01); *A61L 2420/02* (2013.01)

(58) Field of Classification Search
None
See application file for complete search history.

(56) References Cited

U.S. PATENT DOCUMENTS

| | | | |
|---|---|---|---|
| 4,453,939 A | 6/1984 | Zimmerman | |
| 4,655,211 A | 4/1987 | Sakamoto | |
| 4,891,359 A | 1/1990 | Saferstein et al. | |
| 5,605,541 A | 2/1997 | Holm | |
| 5,814,022 A | 9/1998 | Antanavich et al. | |
| 6,599,627 B2 | 7/2003 | Yeo et al. | |
| 6,652,840 B1 | 11/2003 | Prevendar | |
| 6,797,260 B1 | 9/2004 | Prevendar | |
| 7,109,163 B2 | 9/2006 | Pendharkar et al. | |
| 7,824,601 B1 | 11/2010 | Stankus et al. | |
| 8,815,832 B2* | 8/2014 | Wang | A61L 26/0023 536/57 |
| 8,961,544 B2 | 2/2015 | Komlos et al. | |
| 9,028,851 B2 | 5/2015 | Wang et al. | |
| 9,149,511 B2 | 10/2015 | Wang et al. | |
| 9,539,358 B2 | 1/2017 | Wang | |
| 9,717,820 B2 | 8/2017 | Wang et al. | |
| 9,833,541 B2 | 12/2017 | McCoy et al. | |
| 10,034,957 B2 | 7/2018 | Wang | |
| 2002/0192271 A1 | 12/2002 | Hedner et al. | |
| 2007/0083155 A1 | 4/2007 | Muller | |
| 2007/0086958 A1 | 4/2007 | Drake et al. | |
| 2012/0021058 A1 | 1/2012 | Goessl | |
| 2012/0071884 A1 | 3/2012 | Cooper et al. | |
| 2012/0164224 A1 | 6/2012 | Wang et al. | |
| 2012/0302640 A1 | 11/2012 | Macalister | |
| 2014/0005636 A1 | 1/2014 | Wang et al. | |
| 2014/0329769 A1 | 11/2014 | Wang et al. | |
| 2014/0369991 A1 | 12/2014 | Schutte et al. | |
| 2015/0017225 A1 | 1/2015 | Hubbell | |
| 2015/0125537 A1 | 5/2015 | Goh et al. | |
| 2015/0374929 A1 | 12/2015 | Hyde et al. | |
| 2016/0074602 A1 | 3/2016 | Wang et al. | |
| 2016/0114112 A1 | 4/2016 | Riebman et al. | |
| 2017/0128619 A1* | 5/2017 | Ilan | A61P 31/00 |
| 2019/0015546 A1 | 1/2019 | Larsen | |
| 2019/0134258 A1* | 5/2019 | Wang | A61L 26/0066 |

FOREIGN PATENT DOCUMENTS

| | | |
|---|---|---|
| CN | 102451499 | 5/2012 |
| CN | 105148317 A | 12/2015 |
| CN | 105727345 A | 7/2016 |
| CS | 201400005 A3 | 7/2015 |
| EP | 1952828 B1 | 3/2016 |
| EP | 3019205 A1 | 5/2016 |
| EP | 1786480 B1 | 9/2016 |
| MX | 2018005783 A | 4/2019 |
| WO | WO 2003055531 | 7/2003 |
| WO | 2011151386 A1 | 12/2011 |
| WO | WO 2012039592 | 3/2012 |
| WO | 2015013106 A1 | 1/2015 |
| WO | WO2017/077526 A1 | 5/2017 |

OTHER PUBLICATIONS

International Search Report dated Jul. 19, 2021 for Application No. PCT/IB2021/056499.
Sheikhzadeh et al, "The Effect of a New Syringe Design on the Ability of Rheumatoid Arthritis Patients to Inject a Biological Medication", 2012, Applied Ergonomics, vol. 43, pp. 368-375.
Vo et al., "The Biomechanics and Optimization of the Needle-Syringe System for Injecting Triamcinolone Acetonide into Keloids", Journal of Medical Engineering, 2016, 8 pages.
Astin, "Finger Force Capability: Measurement and Prediction Using Anthropometric and Myoelectric Measures", Blacksburg, VA, USA: Faculty of the Virginia Polytechnic Institute and State University of Science Thesis, 1999, 103 Pages.
International Search Report and Written Opinion relating to International Patent Application No. PCTIB2018058681.

* cited by examiner

*Primary Examiner* — Danah Al-Awadi
(74) *Attorney, Agent, or Firm* — David R. Crichton; Leo B. Kriksunov (57) ABSTRACT

The present invention relates to a hemostatic absorbable composition, comprising: a flowable plurality of separate aggregates each comprising: a plurality of absorbable carrier particles coated on a surface thereof by a plurality of smaller particles comprising an absorbable supplemental hemostasis-promoting agent. In some embodiments, the absorbable carrier particles comprise gelatin or collagen, and the supplemental hemostasis-promoting agent comprises oxidized cellulose, oxidized regenerated cellulose, carboxylic oxidized cellulose, carboxylic oxidized regenerated cellulose, thrombin, or tranexamic acid.

9 Claims, 6 Drawing Sheets

HEMOSTATIC COMPOSITE AGGREGATE MATERIALS HAVING SURFACE ENRICHED WITH HEMOSTATIS-PROMOTING AGENTS

FIELD OF THE INVENTION

The present invention relates to a hemostatic absorbable composition comprising: a flowable plurality of separate aggregates each comprising: a plurality of absorbable carrier particles coated on a surface thereof by a plurality of smaller particles comprising an absorbable supplemental hemostasis-promoting agent. In some embodiments, the absorbable carrier particles comprise gelatin or collagen, and the supplemental hemostasis-promoting agent comprises oxidized cellulose, oxidized regenerated cellulose, thrombin, or tranexamic acid.

BACKGROUND OF THE INVENTION

In a wide variety of circumstances, animals, including humans, can suffer from bleeding due to wounds or during surgical procedures. In some circumstances, the bleeding is relatively minor, and normal blood clotting functions in addition to the application of simple first aid are all that is required. In other circumstances, substantial bleeding can occur. These situations usually require specialized equipment and materials as well as personnel trained to administer appropriate aid. Bleeding during surgical procedures may manifest in many forms. It can be discrete or diffuse from a large surface area. It can be from large or small vessels, arterial (high pressure) or venous (low pressure) of high or low volume. It may be easily accessible or it may originate from difficult to access sites. The control of bleeding is essential and critical in surgical procedures to minimize blood loss, to reduce post-surgical complications, and to shorten the duration of the surgery in the operating room.

Conventional methods to achieve hemostasis include use of surgical techniques, sutures, ligatures or clips, and energy-based coagulation or cauterization. When these conventional measures are ineffective or impractical, adjunctive hemostasis techniques and products are typically utilized. The selection of appropriate methods or products for the control of bleeding is dependent upon many factors, which include but are not limited to bleeding severity, anatomical location of the source and the proximity of adjacent critical structures, whether the bleeding is from a discrete source or from a broader surface area, visibility and precise identification of the source and access to the source.

To address the above-described problems, materials have been developed for controlling excessive bleeding. Topical Absorbable Hemostats (TAHs) are widely used in surgical applications. TAHs encompass products based on oxidized cellulose (OC), oxidized regenerated cellulose (ORC), gelatin in various forms with or without a thrombin solution, collagen, chitin, chitosan, etc. To improve the hemostatic performance, scaffolds based on the above materials can be combined with biologically-derived clotting factors, such as thrombin and fibrinogen.

One of the most commonly used topical hemostatic agents is SURGICEL® Original absorbable hemostat, made from oxidized regenerated cellulose (ORC). ORC was introduced in 1960 as a safe and effective hemostatic agent for many surgical procedures. ORC fabric has a loose knit in its matrix structure and conforms rapidly to its immediate surroundings and is easier to manage than other absorbable agents because it does not stick to surgical instruments and its size can be easily trimmed. This allows the surgeon to hold the cellulose firmly in place until all bleeding stops.

Due to its biodegradability and its bactericidal and hemostatic properties, oxidized cellulose, as well as oxidized regenerated cellulose has long been used as a topical hemostatic wound dressing in a variety of surgical procedures, including neurosurgery, abdominal surgery, cardiovascular surgery, thoracic surgery, head and neck surgery, pelvic surgery and skin and subcutaneous tissue procedures. Many methods for forming various types of hemostats based on oxidized cellulose materials are known, whether made in powder, woven, non-woven, knit, and other forms. Currently utilized hemostatic wound dressings include knitted or non-woven fabrics or powders comprising oxidized regenerated cellulose (ORC), which is oxidized cellulose with increased homogeneity of the cellulose fiber.

SURGICEL® absorbable hemostats are used adjunctively in surgical procedures to assist in the control of capillary, venous, and small arterial hemorrhage when ligation or other conventional methods of control are impractical or ineffective. The SURGICEL family of absorbable hemostats consists of four main product groups, with all hemostatic wound dressings commercially available from Ethicon, Inc., Somerville, N.J., a Johnson & Johnson Company:

SURGICEL Original hemostat is a white fabric with a pale-yellow cast, this material is strong and can be sutured or cut without fraying;

SURGICEL NU-KNIT® absorbable hemostat is like Original but has a denser knit and thus a higher tensile strength, this material is particularly recommended for use in trauma and transplant surgery as it can be wrapped or sutured in place to control bleeding;

SURGICEL FIBRILLAR™ absorbable hemostat form has a layered structure that allows the surgeon to peel off and grasp with forceps any amount of material needed to achieve hemostasis at a bleeding site, may be more convenient than the knitted form for hard to reach or irregularly shaped bleeding sites and is particularly recommended for use in orthopedic/spine and neurological surgery;

SURGICEL SNoW™ absorbable hemostat form of the product is a structured non-woven fabric that may be more convenient than other forms for endoscopic use due to the structured, non-woven fabric and is highly adaptable and recommended in both open and minimally invasive procedures.

SURGICEL Powder Absorbable Hemostat a powdered adjunctive hemostat made of aggregates of ORC fiber fragments.

Protein-based hemostatic materials, such as collagen and gelatin, are commercially available in solid sponge, fibrillar and loose or unpacked powder form for use in surgical procedures. Mixing of the loose or unpacked powder with a fluid such as saline or thrombin may form a paste or slurry that is useful as a hemostatic composition for use in cases of diffuse bleeding, particularly from uneven surfaces or hard to reach areas, depending on mixing conditions and relative ratios of the materials.

Gelatin-based hemostats, both in solid sponge or powder form, are commercially available and are used in surgical procedures. Gelatin powder, when mixed with fluid, can form a paste or slurry that is useful as a flowable, extrudable and injectable hemostat for diffuse bleeding, particularly from uneven surfaces or hard to reach areas. The conventional slurry is prepared at the point of use by mechanical agitation and mixing of the powder and liquid to provide uniformity of the composition.

Hemostatic flowable paste (such as gelatin particles mixed with and or dispersed in water or aqueous solutions) is frequently homogeneously mixed with an additional or supplemental hemostatic agent (such as thrombin) that activates, initiates, accelerates or otherwise enhances the efficacy of the hemostatic cascade once in contact with blood plasma prior to administration onto a wound. The additional hemostatic agent, which is consequently largely contained within the bulk of the paste, is not exposed to the bleeding wound surface at the earliest possible time. The additional hemostatic agent which is in the bulk of the paste thus may not be able to immediately contribute to hemostatic biologic processes on bleeding surfaces, potentially adding to unnecessary costs and need to absorb the agent which was not timely available for hemostasis.

SURGIFLO® Hemostatic Matrix Kit, available from Ethicon, Inc., Somerville, NJ, contains SURGIFLO hemostatic gelatin matrix with thrombin and provides a matrix for platelet adherence, accelerating the formation of the platelet plug and aids in fibrin clot formation. It contains EVITHROM® Thrombin, Topical (Human), a lyophilized powder form of thrombin for reconstitution in solution, which can be combined with an absorbable hemostatic gelatin to form a flowable matrix or absorbable gelatin paste intended for haemostatic use by applying to a bleeding surface. The gelatin paste is supplied in a pre-filled syringe to be homogenously mixed with two (2) milliliters of an additional liquid (sterile saline solution or thrombin).

U.S. Published Patent Application No. 2019/0134258 "Hemostatic Paste Having Surface Enriched With Hemostasis-Promoting Agents And Devices For Delivery" discloses a hemostatic semi-solid paste material comprising: a) a bioabsorbable carrier hemostatic material; and b) a supplemental hemostatic agent; wherein the paste material has an elongated form extending along a lengthwise axis with an aspect ratio of at least 3, the paste material is self-supporting and syringe extrudable, and the supplemental hemostatic agent has a non-homogenous distribution profile across a cross-section taken across the lengthwise axis.

U.S. Pat. No. 10,034,957 "Compacted Hemostatic Cellulosic Aggregates" discloses a method of making a plurality of hemostatic aggregates comprising the steps of: a) milling a cellulosic source material to form fibers; b) humidifying the fibers to water content of between 11.0% and 20% by weight; c) roller compacting the fibers to form hemostatic aggregates; d) sieving the hemostatic aggregates; e) dehumidifying the hemostatic aggregates to a moisture content of less than 5.5% determined by loss on drying; and f) optionally dosing the resulting hemostatic aggregates into storage containers or into delivery devices.

U.S. Pat. No. 9,539,358 "Oxidized Regenerated Cellulose Hemostatic Powders And Methods Of Making" discloses a hemostatic material comprising a roller compacted ORC powder comprising particles having average aspect ratio from about 1 to about 18 having a particle size greater than 180 micron and tapped density of at least 0.44 g/mL.

European Patent EP1952828B1 "Hemostatic Textile Material" discloses a hemostatic textile material to stop bleeding comprising: a dialdehyde cellulose (DAC) carrier wherein the degree of oxidation of the dialdehyde cellulose varies from 1.5% to 12%; and a blood coagulation factor selected from chitosan and gelatin; said blood coagulation factor being chemically immobilized thereon; and optionally further comprising: a bacteriolytic agent selected from a lysozyme enzyme, silver nitrate, and chlorhexidine; and further optionally comprising: a selected component that prevents hemolysis, said component selected from tranexamic acid and ε-aminocaproic acid chemically immobilized thereon, wherein the aldehydic groups are spread equally and uniformly onto and into said carrier to allow only 85-90% covalent bonding with amino groups of said blood coagulation factor.

U.S. Pat. No. 6,797,260 "Bleeding Control And Healing Aid Compositions And Methods Of Use" discloses a method of making an improved hemostatic composition comprising the steps of: preparing a slurry comprising (a) a hemostatic agent selected from the group consisting of ferric sulfate, ferric subsulfate and mixtures thereof; (b) aluminum chloride; (c) aluminum ammonium sulfate; and (d) regenerated oxidized cellulose; preparing a substantially dry composition by dehydrating said slurry; and, preparing a paste composition by adding sufficient solvent to said dry composition to reconstitute said dry composition into a paste like consistency.

U.S. Published Patent Application No. 2012/0302640 "Oral Formulations" discloses a topical oral formulation comprising, in the form of a gel, 1 to about 70% by weight tranexamic acid, an antibacterial agent and having a viscosity of about 100 to about 15,000 cP and further a composition wherein the gel is a polysaccharide gel, a cellulosic gel, a methyl cellulosic gel, a hydrogel, agarose, or gelatin or a combination of any two or more thereof.

European Patent EP1786480B1 "Haemostatic Composition Comprising Hyaluronic Acid" discloses a hemostatic composition comprising gelatin and hyaluronic acid or a derivative thereof, wherein said hyaluronic acid or derivative thereof, is incorporated into said composition to a final content of at least 10% (w/w) hyaluronic acid, wherein said composition does not comprise a chemical cross-linking agent or residues thereof, and wherein said composition is obtained by treating a mixture of gelatin, hyaluronic acid or a derivative thereof and a solvent with dry heat at a temperature of from 110 to 200° C.

Published PCT Patent Application No. WO2015/013106A1 "Bone Paste Compositions And Methods Of Using The Same" discloses a thrombogenic bone paste composition, comprising: a) a matrix material; b) a plurality of nanoparticles, said nanoparticles comprising at least one antibiotic agent, at least one growth factor, or a combination of at least one antibiotic agent and at least one growth factor; and c) at least one hemostatic agent.

U.S. Published Patent Application No. 2015/0017225 "Hemostatic Pad Assembly Kit And Method" discloses a hemostatic wound treatment device comprising: a bioabsorbable scaffold having a wound facing surface and an opposing surface; said scaffold wetted with a biocompatible liquid that is not blood or plasma; and a hemostatic powder that adheres by moisture to at least the wound facing surface of said bioabsorbable scaffold.

U.S. Pat. No. 8,961,544 "Dry Composition Wound Dressings And Adhesives Comprising Gelatin And Transglutaminase In A Cross-Linked Matrix" relates to patches comprising dry gelatin compositions.

Chinese Patent Publication No. CN105148317A "Hemostatic Implant" relates to a hemostatic implant, characterized in that the gelatin sponge is a gelfoam sponge soaked with a tranexamic acid by injection.

Chinese Patent Publication No. CN105727345A "Absorbable Hemostasis Film Material And Preparation Method Thereof" discloses an absorbable hemostasis film material, wherein the main components thereof comprise starch, carboxymethyl cellulose and gelatin, wherein weight ratio of the starch, the carboxymethyl cellulose and the gelatin is (1-4):(1-2):(1-3).

Czech Patent Publication No. CZ201400005A3 "Composition For Preparing Modified Gelatin Nanofilaments, Nanofilaments And Process Of Their Preparation" discloses a modified gelatin nanofilament preparing composition comprises gelatin, oxidized cellulose and/or salt of oxidized cellulose with alkali metal, alkaline earth metal or ammonium, and a solvent comprising formic acid and/or acetic acid, where weight ratio of the salt of the oxidized cellulose or oxidized cellulose to gelatin is 0.1-2.

While certain hemostatic materials, such as gelatin, oxidized cellulose and starch, in particle form are known, simply mixing these particles together results in separating mixtures, due to different physicochemical properties, and does not providing improvement in the hemostatic properties. There is a need in hemostatic materials in particulate forms for delivery and uniform coverage of the wound site, where such materials have a high hemostatic efficacy, adherence, deliverability, and speed of action.

SUMMARY OF THE INVENTION

The present invention relates to a hemostatic absorbable composition, comprising: a flowable plurality of separate aggregates each comprising: a plurality of absorbable carrier particles coated on a surface thereof by a plurality of smaller particles comprising an absorbable supplemental hemostasis-promoting agent. In some embodiments, the absorbable carrier particles comprise gelatin or collagen, and the supplemental hemostasis-promoting agent comprises oxidized cellulose, oxidized regenerated cellulose, thrombin, or tranexamic acid. In some embodiments, the supplemental hemostasis promoting agent is present exclusively or primarily on an outside surface of the carrier particles or in an outside layer of the carrier particles, and an internal portion of the carrier particles contains substantially no supplemental hemostasis-promoting agent.

In some embodiments, the supplemental hemostasis-promoting agent comprises oxidized regenerated cellulose and the absorbable carrier particles comprise gelatin, wherein a mass ratio of ORC:gelatin is higher than 10:1; higher than 17:1; or is from 17:1 to 30:1.

In some aspects, the present invention relates to methods of making the hemostatic absorbable compositions, comprising the steps of: hydrating the absorbable carrier particles; mixing the hydrated absorbable carrier particles with the smaller particles comprising the absorbable supplemental hemostasis-promoting agent; forming a mixture with the smaller particles comprising the absorbable supplemental hemostasis-promoting agent adhering to the absorbable carrier particles; drying the mixture; sieving the mixture.

In some aspects, the present invention relates to a method of treating a wound comprising the step of applying the hemostatic absorbable compositions described herein onto and/or into the wound of a patient.

DETAILED DESCRIPTION

According to an embodiment of the present invention, hemostatic absorbable composite powder or aggregate material comprises solid particulates comprising core or scaffold or carrier particles made of a first hemostatic agent, with the surface of said core or scaffold or carrier particles enriched or coated with a second or supplemental hemostasis-promoting agent. The supplemental agent is exposed on the surface of the inventive particulates and is present predominantly as a coating or a layer on the outside of the core particles and is preferably extending outside of the core particles. The supplemental agent is exclusively or primarily positioned on an outside surface of the core particles or in an outside layer of the core particles. A portion of the supplemental agent can be embedded into the surface of the core particles.

Figure 1:
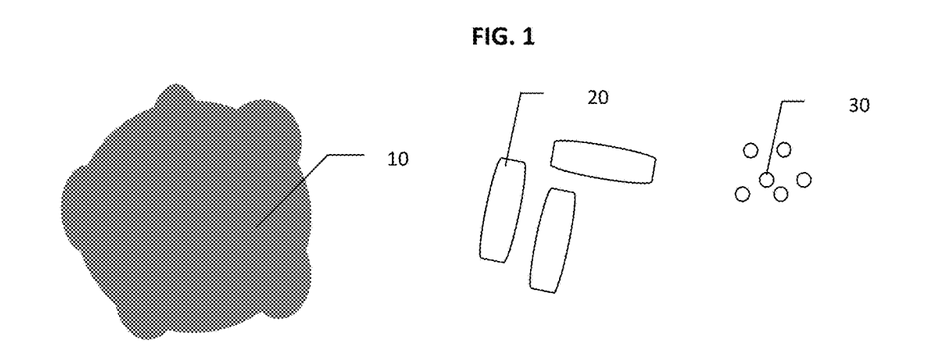
FIG. 1 shows schematic cross-sectional views of components of the present invention.

Referring to FIG. 1, a schematic representation of the components used to make the inventive hemostatic absorbable powder or aggregates material is shown in a schematic cross-sectional view, with relatively larger carrier particles 10, and supplemental hemostasis-promoting agent in the form of relatively smaller supplemental particles 20 and 30, such as elongated particles 20, having aspect ratio (length:width or diameter ratio). over 1, such as 2, 3, 5, or more, or in the form of particles 30 having aspect ratio around 1-2. Carrier particles 10 are preferably having aspect ratio of about 1 to 5, more preferably 1 to 3. Carrier particles are discreet solid particles in a form of a powder.

The carrier or core particles 10 are preferably larger than supplemental hemostasis-promoting agent particles 20, 30, such as at least 2, 3, 5, 10, 15, 20, 50, 100, or even 1000 times larger by largest dimension, by diameter, by volume or by weight. In some embodiments, carrier or core particles 10 have the largest dimension of 150, 200, 300, 500, 1000, 2000 microns, while supplemental particles 20 and 30 have the largest dimension of 3, 5, 10, 20, 30, 50, 75, 100 microns. In some embodiments, larger core particles 10 have the largest dimension of 500, 1000, 2000, 3000 microns, while supplemental particles 20 and 30 have the largest dimension of 150, 200, 300 microns.

Figure 2:
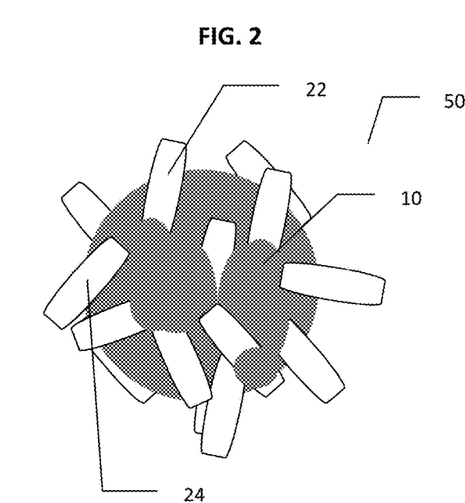
FIG. 2 shows a schematic cross-sectional view of an embodiment of the present invention.

Referring to FIG. 2, a schematic representation of one embodiment of the inventive hemostatic absorbable powder or aggregate material 50 is shown in a schematic cross-sectional view, with carrier particles 10, having on the surface thereof elongated supplemental hemostasis-promoting agent particles 22, 24 that are either partially embedded into carrier particles 10 as shown by elongated supplemental hemostasis-promoting agent particles 22 or attached on the surface of carrier particles 10 as shown by elongated supplemental hemostasis-promoting agent particles 24.

Figure 3:
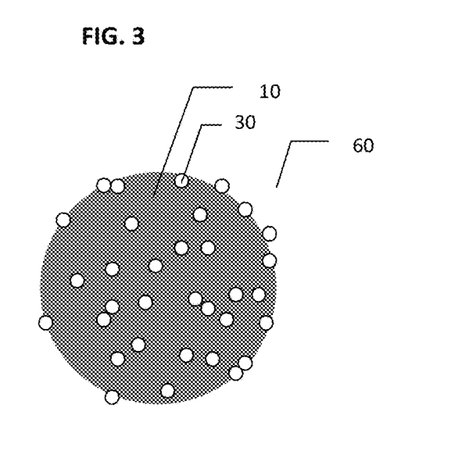
FIG. 3 shows a schematic cross-sectional view of an embodiment of the present invention.

Referring to FIG. 3, a schematic representation of another embodiment of the inventive hemostatic absorbable powder or aggregate material 60 is shown in a schematic cross-sectional view, with carrier particles 10, having on the surface thereof particles 30 either partially embedded into carrier particles 10 or attached on the surface of carrier particles 10.

Figure 4:
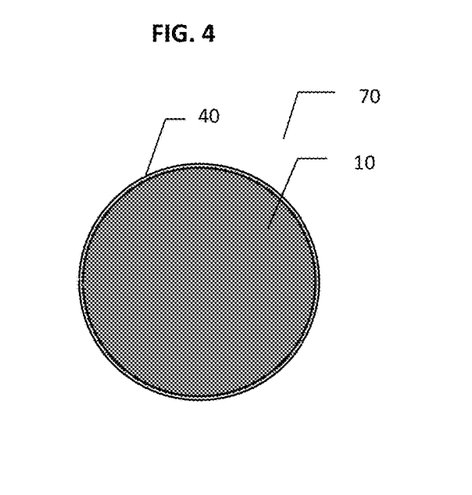
FIG. 4 shows a schematic cross-sectional view of an embodiment of the present invention.

Referring to FIG. 4, a schematic representation of yet another embodiment of the inventive hemostatic absorbable powder or aggregate material 70 is shown in a schematic cross-sectional view, with carrier particles 10, having on the surface a non-particulate coating 40 that comprises supplemental hemostasis-promoting agent.

Advantageously, on average, a larger portion of supplemental hemostasis-promoting agent, in the form of particles 22, 24, 30, or coating 40, is exposed on the surface vs. a smaller portion of particles 22, 24, 30 or coating 40 buried or embedded within core or carrier particles 10. Supplemental hemostasis-promoting agent particles 22, 24, 30 and coating 40 are predominantly present on the surface of hemostatic absorbable powder or aggregate material 50, 60, 70 and thus supplemental hemostasis-promoting agent is more readily available at the wound site for hemostasis, as compared to systems where supplemental hemostasis-promoting agent is homogenously mixed with, and distributed within, carrier or core particles material. Advantageously, the amount of the supplemental hemostasis-promoting agent needed in the inventive embodiments is less when compared to the systems where supplemental hemostasis-promoting agent is homogenously mixed with, and distributed within, carrier or core particles material, due to the ready availability of the supplemental hemostasis-promoting agent on the surface for interactions with blood and tissue at the wound site.

The hemostatic performance of the inventive hemostatic absorbable powder or aggregate material is expected to be better relative to a simple mechanical mix of carrier particles 10 and supplemental hemostasis-promoting agent particles 20, 30; or separate carrier particles 10 and supplemental hemostasis-promoting agent particles 20, 30; or supplemental hemostasis-promoting agent homogenously mixed with, and distributed within, carrier or core particles material. Not only is supplemental hemostasis-promoting agent more bioavailable when present on core particles 10, biomechanics, availability, staying on tissue and sticking to tissue and wound surface for interacting with tissue and blood is improved when very small particles 20, 30 having very large area are supported on larger carrier particles. Conversely, small particles 20, 30, while having excellent surface area and reactivity, are on their own (i.e. not supported on the carrier 10) are a challenge to deliver to the wound. Further, such particles are frequently unable to stay on the wound long enough for effecting hemostasis and are easily removed with blood flow or any other mechanical interference, which is undesirable.

Advantageously, it is postulated that the inventive hemostatic absorbable powder or aggregate material, comprising a given quantity Qc of carrier particles 10 and a given quantity Qh of hemostasis-promoting agent particles 20, 30, with the hemostasis-promoting agent disposed on or in surface layer 54 has the hemostatic performance that is better than performance of a comparative test articles comprising the same given quantities Qc and Qh of respectively carrier particles and hemostasis-promoting agent as follows:
 a. Comparative test article whereby the hemostasis-promoting agent is homogeneously mixed into the material of carrier particles 10 or
 b. Comparative test article whereby the hemostasis-promoting agent is simply mixed with carrier particles 10.

Further, it is postulated that for the inventive test article comprising a given quantity Qc of carrier particles 10 and a given quantity Qh of hemostasis-promoting agent particles 20, 30, with the hemostasis-promoting agent disposed on or in surface layer 54 has the hemostatic performance is equal or better than performance of a comparative test articles comprising a larger quantity of hemostasis-promoting agent, such as 1.25 Qh, 1.5 Qh, 2 Qh, 3 Qh, 5 Qh, whereby such hemostasis-promoting agent is
 a. homogeneously mixed into the material of carrier particles 10 or
 b. simply mixed with carrier particles 10.

Advantageously, according to the present invention, the hemostatic performance is improved when a similar quantity of Qh of hemostatic agent is disposed on or in surface layer 54, comparative to the same quantity Qh of hemostasis-promoting agent that is homogeneously mixed into or with the carrier particles. Additionally, the same hemostatic performance can be achieved with a smaller quantity Qh of hemostatic agent disposed on or in surface layer 54, comparative to the quantity 1.25 Qh or higher of hemostasis-promoting agent homogeneously mixed into or with the carrier particles.

According to the present invention, the presence of hemostasis-promoting agents disposed on or in surface layer 54 provides for faster access of the hemostatic agents to the bleeding site and/or tissue in the first several seconds or minutes when hemostasis is sought; on the contrary the comparative hemostasis-promoting agents that are buried deeply inside carrier particles, and consequently, having less ability to affect hemostasis during the critical first several seconds or minutes when hemostasis is sought.

In one example, carrier particles 10 are represented by gelatin particles and supplemental hemostasis-promoting agent particles 20 are represented by oxidized regenerated cellulose (ORC) powder whereby the inventive hemostatic composite aggregate material 50 exhibits better hemostatic performance relative to a simple mechanical mixture of gelatin carrier particles 10 and ORC based supplemental hemostasis-promoting agent particles 20; or separate gelatin carrier particles 10 and ORC-based supplemental hemostasis-promoting agent particles 20; or ORC based supplemental hemostasis-promoting agent homogenously mixed with, and distributed within, gelatin based carrier or core particles 10.

Advantageously the core particles 10 and the supplemental particles 22, 24, 30, or coating 40 are physically or physiochemically bound and integrated together. Carrier particles 10 are enriched only on the surface thereof with relatively smaller supplemental hemostasis-promoting agent particles or coatings which are exposed on the surface of carrier particles 10.

Materials: Core Particles

Figure 5:
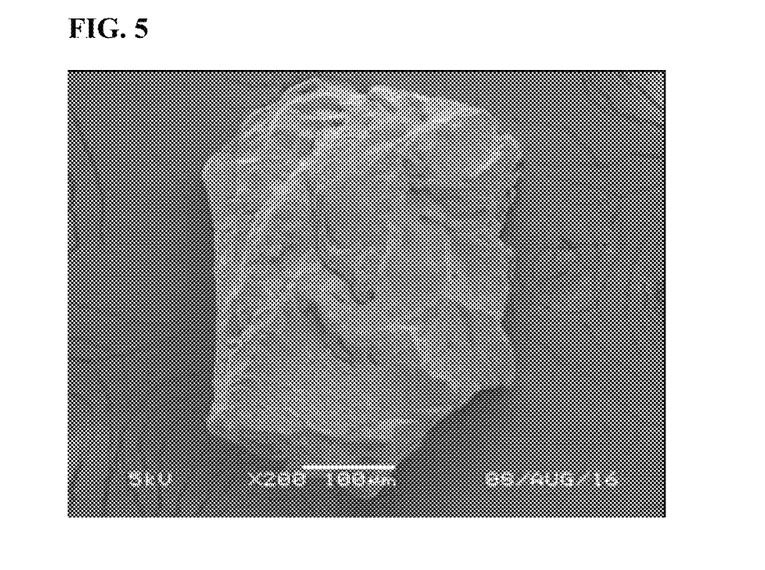
FIG. 5 shows a gelatin particle.

In one embodiment, the carrier or core hemostatic particles 10 comprise gelatin, collagen, or combinations thereof. FIG. 5 shows a typical gelatin particle.

Many sources of gelatin and gelatin powder are available, including WVR catalogs, etc. A gelatin commercially available as SURGIFLO Hemostatic Matrix, available from Ethicon, Inc., Somerville, NJ, comprises sterile, absorbable cross-linked gelatin intended for hemostatic use by applying to a bleeding surface.

Gelatin or collagen particles can be obtained by many techniques known to a skilled artisan. In one embodiment, gelatin can be obtained by milling SURGIFOAM® Absorbable Gelatin Sponge, available from Ethicon, Inc., Somerville, NJ. Another source of gelatin core particles can be SURGIFOAM Absorbable Gelatin Powder Kit, available from Ethicon, Inc., Somerville, NJ.

In some embodiments, gelatin particles can be obtained by milling any medical grade gelatin to an appropriate size.

Materials: Supplemental Hemostatic Agent

The supplemental hemostatic agent 20, 22, 24, 30, 40 comprises any hemostasis-promoting, and/or clotting promoting, and/or platelet aggregation promoting active medicant material, such as enzyme, protein, peptide, molecule, natural material, modified natural material such as oxidized cellulose (OC) or oxidized regenerated cellulose (ORC), solvent extract, or particle, or particle aggregates, and combinations thereof.

U.S. Pat. No. 9,539,358 by Yi-Lan Wang, Guanghui Zhang "Oxidized Regenerated Cellulose Hemostatic Powders And Methods Of Making", which is incorporated by reference herein in its entirety, discloses various ORC coarse and fine fiber particles that can be utilized as supplemental hemostatic agent in practicing the present invention.

U.S. Pat. Nos. 9,717,820; 9,149,511 by Yi-Lan Wang, Guanghui Zhang "Procoagulant Peptides And Their Derivatives And Uses Therefor", incorporated by reference herein, discloses hemostatically active peptides that can be utilized as supplemental hemostatic agent in practicing the present invention.

U.S. Pat. No. 9,028,851 by Yi-Lan Wang et al. "Hemostatic Materials And Devices With Galvanic Particulates" incorporated by reference herein, discloses hemostatically active galvanic particulates that can be utilized as supplemental hemostatic agent in practicing the present invention.

In the preferred embodiments, the supplemental hemostatic agent comprises: (A) oxidized cellulosic particles; (B) oxidized regenerated cellulose particles (C) hemostatically active enzyme, such as thrombin or thrombin equivalent, optionally mixed with an excipient; (D) platelet aggregating peptide; (E) hemostatic solvent extract of a natural material; (F) tranexamic acid; (G) combinations of the above, with optional excipients such as gelatin, polyethylene glycol, carboxymethylcellulose (CMC), or similar.

ORC coarse and fine fiber can be obtained as follows. A reference is made to the U.S. Pat. No. 9,539,358 Oxidized regenerated cellulose hemostatic powders and methods of making, which is incorporated by reference herein in its entirety for all purposes.

One method of obtaining ORC coarse and fine fiber directly from cellulosic materials, such as ORC fabric or non-woven products is as follows.

Briefly, the manufacturing process starts with ORC material, such as SURGICEL Original absorbable hemostat, which is cut into 1- to 2-inch wide sections before the material is fed into a blade that cuts the fabric into smaller pieces. The cut ORC fabric pieces are then ground into intermediate ORC fine fibers by two consecutive milling processes (hammer milling and air classifier milling). In an alternative embodiment, the cut ORC fabric pieces are converted directly into intermediate fine fibers in a ball mill.

More specifically, one process for manufacturing the ORC fine fiber comprises the steps of: a) slitting and cutting of cellulosic source material; b) milling the resulting material from step a); and c) a second milling step in an air classifier.

Slitting and cutting can preferably be performed to slit and cut fabric into appropriate size pieces that are between approximately 1 inch by 3 inches or 2 inches by 3 inches, though smaller pieces can also be used. The main operations performed for slitting and cutting are to unwind a roll of fabric, slit the fabric into strips, cut the strips to size and deliver the cut pieces into the first milling step. Many cutting and slitting machines are known and commercially available, such as AZCO Model FTW-1000 available from AZCO. In the first milling step, processed pieces of cellulosic fabric are converted from an intermediate coarse fiber produced in the slitting and cutting step to a material having a D90 value of less than 452 µm and D50 value of less than 218 µm, while having minimal impact on the color index and water-soluble content of the material. Many machines for milling are commercially available, such as Models DASO6 and WJ-RS-D6A manufactured by Fitzpatrick, which are hammer mill type milling machines, equipped with a 497 micron round screen and a set of blades that breaks down the fabric until it passes through the screen to produce intermediate coarse cellulosic fiber.

In an exemplary processing run, mill speed can be about 7000 RPM; processing temperature at less than 80° C.; screen size between 1534 and 9004; number of blades as 8 (2 impellers each); blade type as a 225 knife, impact type blades; blade orientation set as "impact".

At this stage in the preferred process, the size of the intermediate coarse fiber produced in the first milling step is further reduced to a D90 value of less than 177 µm and a D50 value of less than 95 µm while keeping a minimal impact on the color index and water-soluble content of the material. Many machines are available for second milling step, such as an Air Classifier/F10 Quadro Fine Grind from Quadro.

Intermediate coarse fiber from the first milling step can be fed at a controlled rate into the second mill and passed through two milling chambers that are separated by a milling screen. The material can be pulled through the milling chamber by an air blower. The intermediate coarse fiber can be processed through the air classifier equipment three times to obtain the desired size. At the end of the second milling step, the intermediate fine fiber can be collected.

In an exemplary processing run, a Quadro Air Classifier F10 can be used in the second milling step with a milling speed of 8400 rpm, blower speed of 1800 rpm, 0.0018" round hole screen and 3 passes. ORC intermediate fine fiber can be also produced in one step by ball milling instead of the two steps milling steps as described above. In an alternative ball milling embodiment, 50 g of pre-cut ORC fabric (2 inch×2 inch) is ball milled with 12 high-density Zirconia (zirconium dioxide ZrO2, 20 mm in diameter; Glen Mills Inc., Clifton, N.J., USA) by placing the balls and the samples in a 500-mL grinding jar. The jar is clamped into the latching brackets and then counterbalanced on the planetary ball mill PM100; Retsch, Inc., Newtown, Pa., USA). The milling is then performed bi-directionally at 450 rpm for 20 minutes.

Typical ORC particles useable in practicing the present invention are ORC fine fiber particles that have the aspect ratio or ratio of length to diameter preferably from about 2 to about 100, such as 3 to 50, such as 10, and size of particles from about 10 to about 300 microns, such as 20-200 microns.

Figure 6:
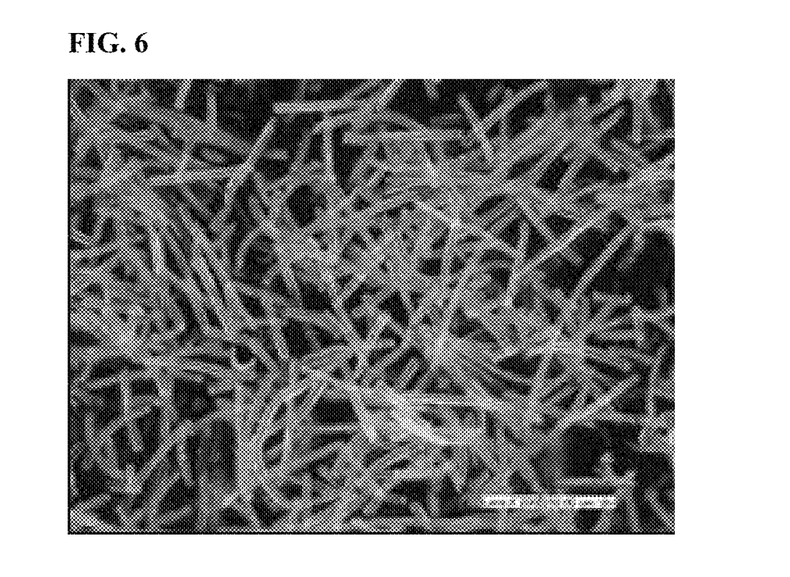
FIG. 6 shows ORC fine fibers.

Referring now to FIG. 6, there are shown ORC fine fibers useful in practicing the present invention.

INVENTIVE EMBODIMENTS WITH ORC COVERED GELATIN CORE

In one embodiment, the carrier or core hemostatic particles 10 comprise gelatin, and the supplemental hemostatic agent 20, 22, 24 comprises elongated ORC fine particles.

The aspect ratio or ratio of length to diameter of ORC fine fibers particles is preferably from about 2 to about 100, such as 3 to 50. Preferably, on average, a larger portion of ORC particles is exposed relative on average to a smaller portion of ORC particles is buried within gelatin. ORC present on the surface is more readily available at the wound site for hemostasis. The amount of ORC needed is comparatively less as only the ORC on the surface of gelatin particle is active for immediate reaction with tissue and blood on the wound. A smaller quantity of ORC should have identical or better hemostatic effects when ORC present on the surface relative to a larger quantity of ORC when homogeneously mixed into the gelatin particles. Hemostatic performance of inventive particles is better relative to a simple mix of gelatin and ORC powders and relative to individual ORC powder and individual gelatin powder. The supplemental hemostatic agent in the form of particles on the surface of core particles 10 is expected to have better and faster reactivity relative to homogenous coatings on the surface of core particles 10 because of larger surface area of the supplemental hemostatic agent available for interactions with blood.

Below there are provided a number of methods of making the inventive hemostatic composite aggregate material. In the preferred embodiments, core particles 10 comprise gelatin or collagen and supplemental hemostatic agent comprises ORC particles, thrombin, tranexamic acid, or combinations thereof.

Method of Making: Example 1A. Hydrated Gelatin Particles+ORC

In one embodiment, gelatin particles are initially hydrated by exposure to a small quantity of water or saline allowing them to absorb some water. The ORC fine particles are then admixed and the components mixed well and then allowed to dry. Optional gentle shredding of any clusters formed, if any, can be then provided.

Method of Making: Example 1B. Gelatin Particles+ORC in Presence of Rapidly Evaporable Solvent Instead of water, as shown in Example 1A, a solvent such as ethanol can be used (gelatin is not soluble in 100% ethanol). In this embodiment, ethanol is used instead of water, or as an ethanol-water mixture.

Method of Making: Example 1C. Ball Milling of Gelatin Particles and ORC

Gelatin particles and ORC fine particle are combined in a ball mill and milled together in controlled, high humidity atmosphere and then allowed to dry. Instead of humid atmosphere, small quantity of water or ethanol (absolute or containing 1-10% water) can be added.

Method of Making: Example 1D. ORC Fabric+Coated with Gelatin and Milled

In this embodiment, ORC non-woven or fabric material is coated with gelatin, the coating is allowed to fully dry, and then the fabric or non-woven is milled or shredded, to result in gelatin/ORC particles with partially exposed ORC on the surface.

Method of Making: Example 1E. Gelatin+Tranexamic Acid

Tranexamic acid (TA) is soluble in water (167 mg/ml), poorly in ethanol (<1 mg/ml). Gelatin particles are mixed with a small quantity of water or ethanol/water mix containing tranexamic acid and then allowed to dry forming a coating of TA on the surface.

Method of Making: Example 1F. Gelatin+Tranexamic Acid

Gelatin particles are hydrated by exposure to a small quantity of water or ethanol/water to absorb some water. TA powder is then admixed and the components mixed well and then allowed to dry. Optional—gentle shredding of any clusters formed, if any.

Method of Making: Example 1G. Gelatin+Tranexamic Acid

Gelatin particles and TA powder are combined in a ball mill and milled together in controlled, high humidity atmosphere and then allowed to dry. Instead of humid atmosphere, small quantity of water or ethanol (absolute or containing water) can be added.

Figure 7:
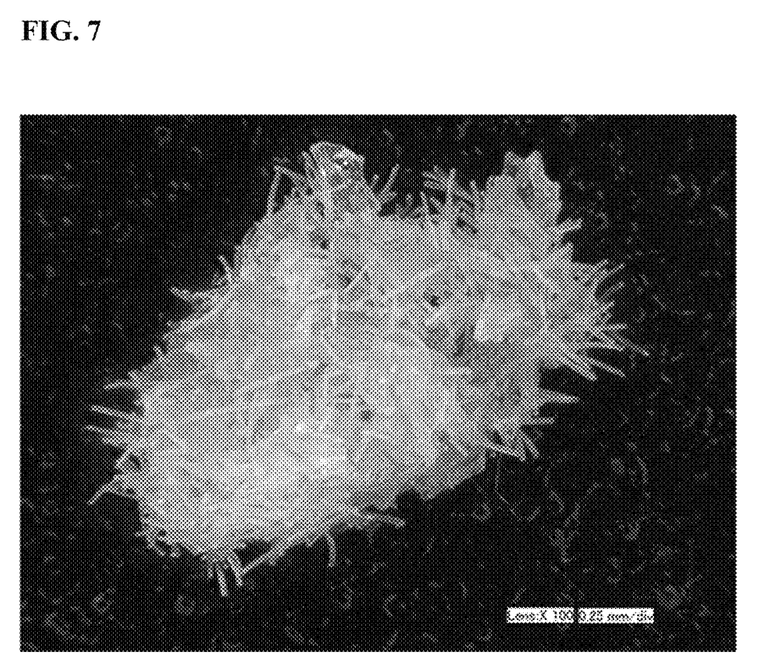
FIG. 7 shows gelatin particles coated with ORC fine fibers.
Figure 8:
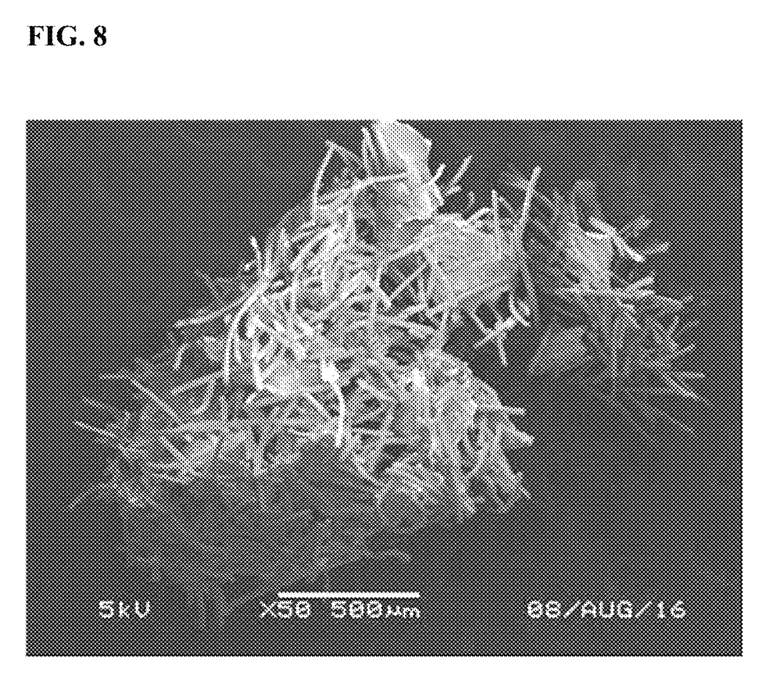
FIG. 8 shows gelatin particles coated with ORC fine fibers.

Referring now to FIGS. 7 and 8, there are shown gelatin particles coated with ORC fine fibers comprising the inventive hemostatic absorbable composite powder or aggregate material, made by the method of Example 1a.

Example 2. Preparation, Characterization, and Testing of Hemostatic Absorbable Composite Aggregate Powder Material for Testing In Vitro Mixing the reagents. Gelatin powder, reagent grade, was obtained from VWR, 9764-500G. The preparation steps included: Weigh approximately 0.1 g of gelatin. Add 500 μl of purified water and mix thoroughly to ensure all gelatin is hydrated. After that, add 1 g of ORC fine fiber and mix by shaking in a sealed container such that the fibers are uniformly dispersed to ensure all gelatin particles are coated. In this example, the initial ratio of gelatin to water to ORC fibers was 1:0.5:10 by weight for the initial mixing (for preparation) and the time elapsed for the mixing process was around 30 seconds. Excess ORC fiber was then removed by sieving (see below). Larger ORC-gelatin particles were also homogenized into smaller particles that were then further coated during the multilayered sieving process. To confirm that all particles are adequately coated, check under a microscope was performed to observe coating ratio (see below for expected characterization).

Drying. Heating Oven: Isotemp (Fisher Scientific, Model: 2001FS) was utilized to remove excess moisture from ORC-coated gelatin particles. The heating oven was heated to 60° C. and the well mixed reagents placed inside. Regular check of the mass of the sample on the balance used until the mass of the sample has stabilized before the following step.

Sieving. Sieves (106 μm, 180 μm, 300 μm) by W. S. Tyler Company (8570 Tyler Boulevard, Mentor, Ohio) were utilized to obtain homogeneous size distributions of the inventive composite aggregate powder material. Place the three sieves on top of each other in order of decreasing size (300 on top, 106 on bottom). Place the composite aggregate powder material samples from the drying step on the top sieve along with the zirconium ball. Zirconium Ball was used to gently grind ORC-gelatin particles clusters into smaller homogeneous pieces. Shake until there are no more large particles on the top sieve layer. The composite aggregate powder material comprising the ORC-coated gelatin particles on the 180 μm layer (sized about 180-300 μm) were then utilized for assessing hemostatic performance as shown below.

Figure 9:
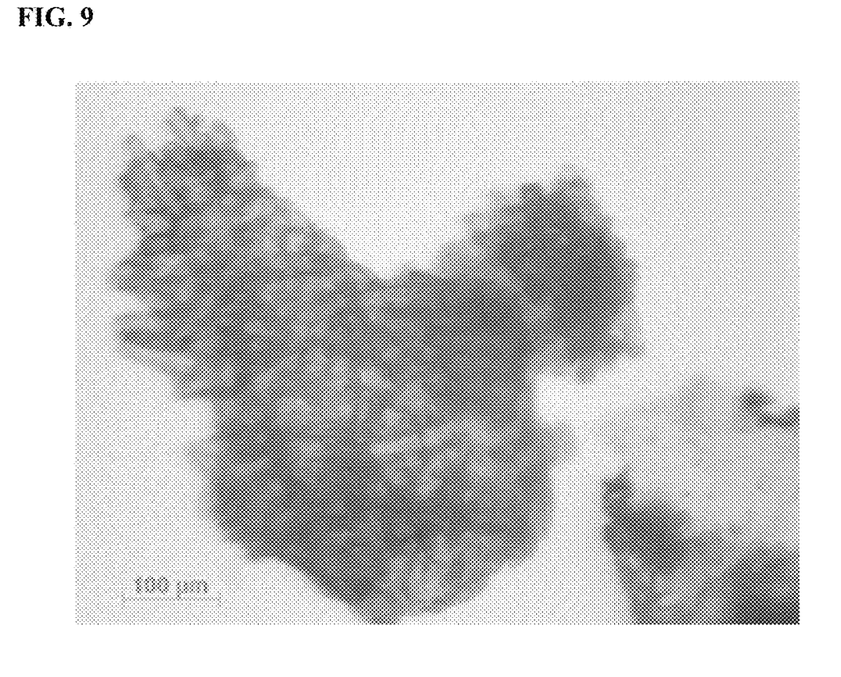
FIG. 9 shows gelatin particles coated with ORC fine fibers.

Characterization. Characterizing the coating ratio of ORC fibers per gelatin particle using optical study under the microscope. Microscope: ZEISS SteREO Discovery. V20, (Carl Zeiss Microscopy, LLC, One North Broadway, White Plains, N.Y.) was used to assess mass ratios of components of ORC-coated gelatin particles. The ORC-coated gelatin aggregates utilized in this Example (180-300 μm diameter) were analyzed under the microscope and found to contain on average 29 ORC fine fibers per 1 gelatin particle. An example of the particle is shown in FIG. 9.

The same weight ratio of gelatin to ORC as above 1:10 was prepared in dry form, with 0.2 g gelatin and 2 g of ORC used. This was also repeated with water to form the ORC-coated gelatin particles and then dried to remove excess moisture before testing, in order to compare initial bulk mass of powder and the final coating ratio.

The number of particles in each bulk mass of ORC and gelatin powders was then counted using the particle size and shape analyzer.

Figure 10:
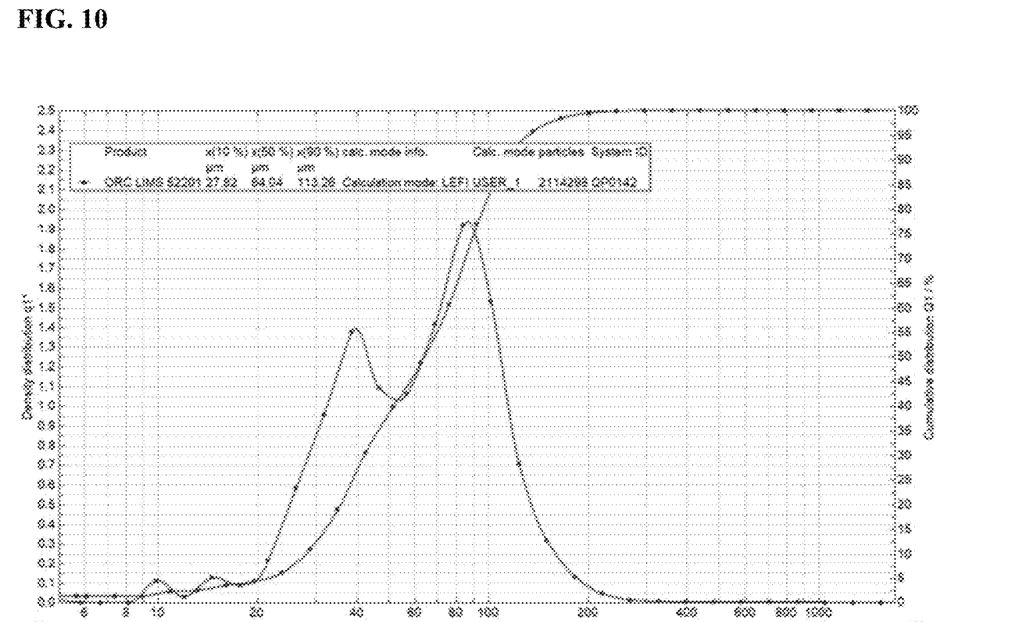
FIG. 10 shows particle size distribution and number of particles vs. particle size in microns for ORC.
Figure 11:
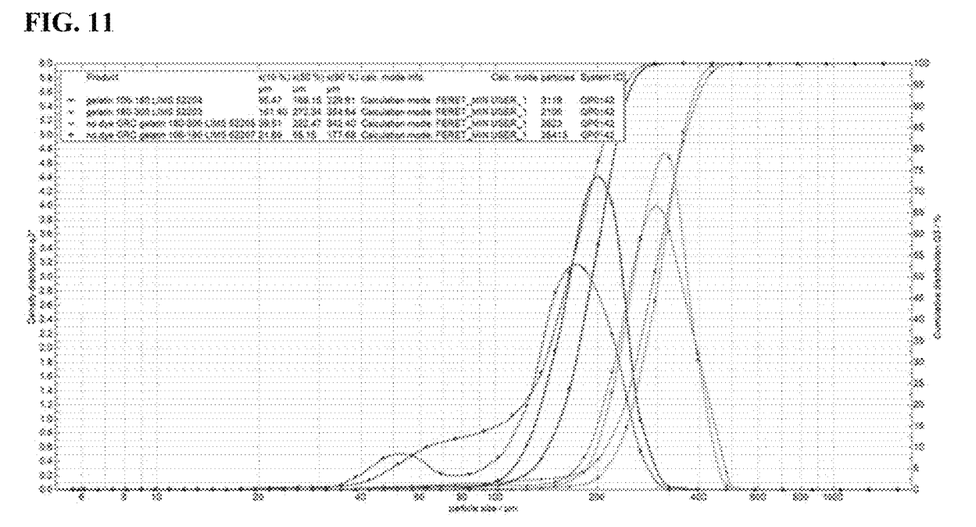
FIG. 11 shows particle size distribution and number of particles vs. particle size in microns for gelatin particles and gelatin coated with ORC fine fibers aggregates.

Number of particles and particle size distribution. The number of ORC fine fibers and gelatin particles are determined for a given mass (2 g and 0.2 g of bulk powders, respectively). The mass ratio was found to be for ORC:gelatin to be 0.289 g:1 g in an average ORC-coated gelatin aggregate. The data was obtained by Particle Size and Shape Analyzer QICPIC Sympatec (Sympatec GmbH, Am Pulverhaus 1, 38678 Clausthal-Zellerfeld, Germany), which was used to count particles and determine the mass ratio of particles within aggregates. Referring to FIGS. 10, 11, particle size distribution and number of particles are plotted relative to particle size in microns for ORC (FIG. 10), gelatin and gelatin coated with ORC fine fibers forming the inventive aggregates (FIG. 11). These figures provide details into the general characterization of the inventive aggregates relative to its individual components, which may play a role in the hemostatic efficacy of the material.

Clotting test. Citrated Human Blood (obtained from Lampire Biological Laboratories, Pipersville, PA, USA, Donor Gender: Male; the blood was aseptically drawn form a normal, healthy, drug-free donor who showed no signs of clotting deficiency) was stored at 2-8° C. prior to use in the vitro clotting test performed as follows.

Remove citrated blood from storage, allow it to warm up and gently shake using an orbital shaker or rotator (Belly Button Orbital Platform Shaker, (Stovall BBUAAUV1S or IBI Scientific™ BBUAAUV1S, Fisher Scientific, Thermo Fisher Scientific Inc. 81 Wyman Street, Waltham, MA) to provide thorough mixing of citrated blood, at room temperature for 60 minutes prior to testing or until the blood is homogeneous in color.

In Vitro Clotting Testing for control samples (no added hemostatic materials) was performed as follows. Weighed the empty vial using a calibrated balance. Added 300 μL of the citrated blood to the vial. Waited 3 minutes to allow clot formation. Weighed the vial filled with blood, and inverted the vial upside down for 1 minute to let any non-clotted blood to flow out of the vial. Firmly tapped the bottom of the vial 5 times after initial inversion. Weighed the vial again with any remaining clotted blood inside and calculated the % mass retained between initial and final measurement, subtracting the mass of the vial. The % of blood retained in the vial after inversion is then used to characterize the efficiency of clotting (high percent corresponding to better clotting)

In Vitro Clotting Testing for test samples (containing added hemostatic materials) was performed as follows. Weighed the empty vial using a calibrated balance. Prepared 0.02 g of the appropriate sample using a calibrated balance. Added 300 μL of the citrated blood to the vial. Added the test sample to its respective vial afterwards using the micro funnel.

Waited 3 minutes to allow clot formation. Weighed the vial filled with blood and the test sample, and inverted the vial upside down for 1 minute to let any non-clotted blood to flow out of the vial. Firmly tapped the bottom of the vial 5 times after initial inversion to remove excess material and reduce false clotting due to adhesive forces between the blood and vial walls. Weighed the vial again with any remaining clotted blood inside and calculated the % mass retained between initial and final measurement, subtracting the mass of the vial. The % of blood retained in the vial after inversion is then used to characterize the efficiency of clotting (high percent corresponding to better clotting). Repeated steps for each test sample and recorded the % mass of blood retained (i.e. clotted). One sample from each test group incl control was tested for clotting efficacy simultaneously to minimize variability in experimental setting. At least 4 trials were performed to reduce variability within each experimental trial.

Each trial of testing was also performed on four samples of citrated blood, adding a different combination of ORC and gelatin to each sample. These samples were used to compare the in vitro clotting efficacy of ORC-coated gelatin relative to other test articles under similar conditions. These four (4) samples were also compared to a control group, which consisted of four (4) samples of citrated human blood without any test articles added to it. At least 4 trials were performed to minimize experimental variability.

Each test article was applied at 20 mg/300 μL of blood for all samples except those in the Control group. This ratio was selected to be clinically relevant and adequately capture clotting performance.

One sample from each test group and control was used for each trial in order to reduce variability.

Figure 12:
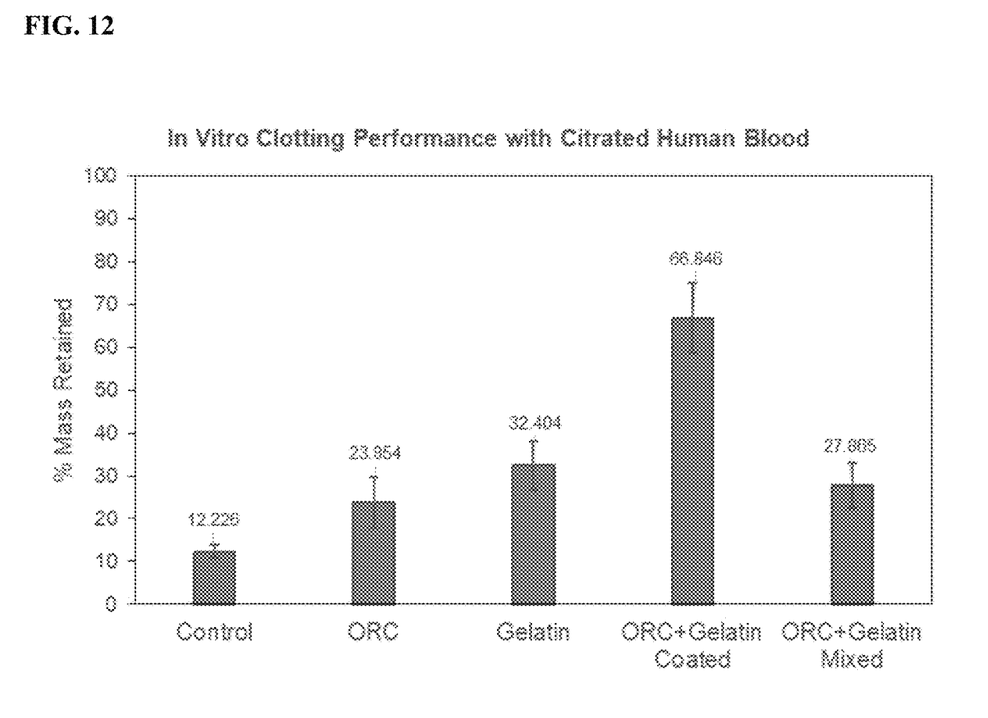
FIG. 12 shows comparative results of in vitro clotting testing.

Referring now to FIG. 12, the results of the in vitro clotting tests are shown. The highest mass retained, indicating most clotting in a given time, was observed with the inventive ORC/gelatin aggregates. The individual materials tested, ORC, gelatin, as well as a physical mix of ORC and gelatin which are not formed into the inventive composite ORC/gelatin aggregates) shows lower retained mass and thus shows lower hemostatic or clotting performance vs. the inventive composite ORC/gelatin aggregates. The lowest mass retained was observed, as expected, for blood without any additions of hemostatic materials (control). The results indicate significant synergistic effect acceleration clotting for the inventive composite ORC/gelatin aggregates.

Example 3. Electro-Mechanical Clotting Characterization

In vitro clotting/gelation performance was determined by an electro-mechanical clot detection method (viscosity-based detection system) to measure the clotting/gelation times for various weights of the test materials with re-calcified citrated human blood. This in vitro clotting/gelation performance was evaluated with the use of a coagulometer Diagnostica Stago ST4 coagulation analyzer (Diagnostica Stago Inc., 5 Century Drive, Parsippany, NJ or Diagnostica Stago S.A.S. 3 allée Thérésa, CS 10009, 92665 Asnières sur Seine Cedex, France).

Test materials were applied at 5 mg/200 µL except those in the Control group (no added hemostatic materials to the blood samples). The ratio of the test materials to blood was evaluated prior to executing this in vitro clotting test.

Citrated human blood was removed from the storage, allowed to warm up, and gently shaken using an orbital rotator at room temperature for 60 minutes prior to testing. The citrated human blood was purchased from Lampire Biological Laboratories, Pipersville, PA, USA. The blood was aseptically drawn from a normal, healthy, drug-free male donor who showed no signs of clotting deficiency.

Calibration was performed on the benchtop coagulometer prior to testing, and followed a manual of Neoplastine CI PLUS STA. The PT time of Abnormal Control was obtained between 33-48 seconds, and the PT time of Normal between 11.5-15.5 seconds.

0.02M $CaCl_2$ saline stock solution [1.33 µL of 1M standard $CaCl_2$ (Fluka Analytical) solution in 65.33 µL saline (0.9% Sodium Chloride Irrigation, USP, Baxter Healthcare Corporation] was prepared. 66.67 µL of 0.02M $CaCl_2$ saline stock solution was added to each cuvette containing 1 iron ball and cuvettes were placed in the incubation area for pre-warming at 37° C. for at least 60 seconds. 133.33 µL of the citrated human blood was then added to the cuvette, followed by immediately adding a pre-weighed test material via a micro funnel (QOSMEDIX 20038, 0.78 in×0.83 in) into each cuvette and pressing start button to initiate test. No test material was added to blood for the Control group. Clotting time was recorded for each application.

Figure 13:
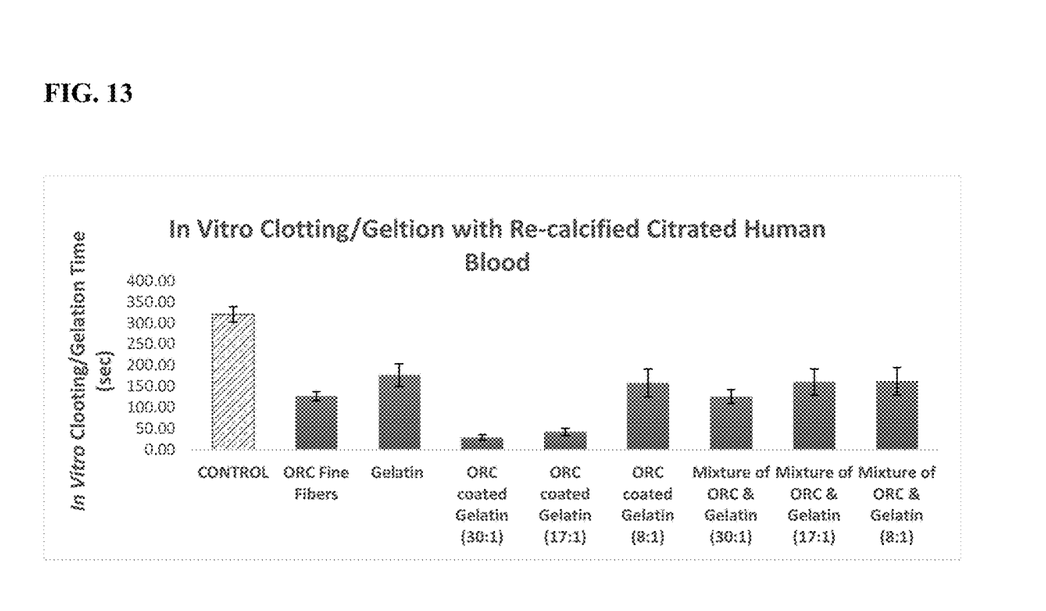
FIG. 13 shows comparative results of in vitro clotting testing.

Referring now to FIG. 13, the results of the testing are presented. As shown, the results indicate that the inventive composite ORC/gelatin aggregates show faster in vitro clotting/gelation times, overall faster than 50 seconds for aggregates by mass ratio 17:1 and 30:1 ORC/gelatin and faster than 25 seconds for 30:1 ORC/gelatin. The clotting/gelation of these aggregates is much faster than observed for comparative mixtures (not aggregates) of ORC and gelatin with the same quantities and ratios of materials, showing times in excess of 100 or 150 seconds, respectively. Similarly, pure ORC and pure gelatin exhibited slow clotting/gelation times in excess of 100 or 150 seconds, respectively. Control (with no additive hemostatic material) showed, as expected, the longest time to clotting, in excess of 300 seconds. Notably, 8:1 ORC/gelatin aggregates have not showed any improvement over comparative mixture (not aggregates) of ORC and gelatin with the same quantities and ratios of materials, i.e. 8:1, with time to clotting of about 150 s for both aggregates form and comparative mixture. The experimental data indicates a significant synergistic effect and improvements in hemostatic effects for the inventive composite ORC/gelatin aggregates, particularly for aggregates having ratios above 8:1, such as above 10:1, or such as above 15:1, such as 18:1, 30:1, and above.

While the invention has been described above with reference to specific embodiments thereof, it is apparent that many changes, modifications, and variations can be made without departing from the inventive concept disclosed herein. Accordingly, it is intended to embrace all such changes, modifications, and variations that fall within the spirit and broad scope of the appended claims.

We claim:

1. A hemostatic absorbable composition, comprising:
a flowable plurality of dry separate aggregates each aggregate being an absorbable carrier particle having a first size dimension, that is coated on a surface thereof by a plurality of hemostasis-promoting particles comprising a supplemental hemostasis promoting agent, having a size dimension smaller than the first size dimension, wherein the supplemental hemostasis-promoting agent comprises oxidized regenerated cellulose (ORC) and the absorbable carrier particles comprise gelatin, wherein a mass ratio of ORC: gelatin is greater than 10:1.

2. The hemostatic absorbable composition of claim 1, wherein the supplemental hemostasis promoting agent is present exclusively or primarily on an outside surface of the carrier particles or in an outside layer of the carrier particles.

3. The hemostatic absorbable composition of claim 1, wherein an internal portion of the carrier particles contains substantially none of said supplemental hemostasis-promoting agent.

4. The hemostatic absorbable composition of claim 1, wherein the separate aggregates have average dimensions between 100 and 500 microns.

5. The hemostatic absorbable composition of claim 1, wherein the absorbable carrier particles comprise thermally cross-linked gelatin.

6. The hemostatic absorbable composition of claim 1, wherein the supplemental hemostasis-promoting agent comprises oxidized regenerated cellulose in a form of a fine elongated particles having aspect ratio on average of at least 3 or higher.

7. The hemostatic absorbable composition of claim 1, wherein the absorbable carrier particles comprise particles having an aspect ratio on average of lower than 3.

8. The hemostatic absorbable composition of claim 1, wherein the mass ratio of ORC:gelatin is greater than 17:1.

9. The hemostatic absorbable composition of claim 8, wherein the mass ratio of ORC:gelatin is from about 17:1 to 30:1.

* * * * *